United States Patent [19]

Rousset et al.

[11] Patent Number: 4,803,291

[45] Date of Patent: Feb. 7, 1989

[54] PARTICULATE COMPOSITIONS OF FERROMAGNETIC METAL OXALATES IN THE FORM OF SUBMICRONIC ACICULAR PARTICLES, THE PREPARATION OF SAME AND APPLICATION THEREOF

[75] Inventors: Abel Rousset, Ramonville St Agne; Christiane B. Salvaing, Toulouse; Paul Mollard, Domene; Alain Manoux, Corbeil Essones; Philippe Tailhades, Mazamet, all of France

[73] Assignees: Centre National de la Recherche Scientifique, Paris; Universite Paul Sabatier, Toulouse, both of France

[21] Appl. No.: 62,941

[22] PCT Filed: Sep. 30, 1986

[86] PCT No.: PCT/FR86/00338

§ 371 Date: Jul. 2, 1987

§ 102(e) Date: Jul. 2, 1987

[87] PCT Pub. No.: WO87/02033

PCT Pub. Date: Apr. 9, 1987

[30] Foreign Application Priority Data

Sep. 30, 1985 [FR] France ................................. 85 14438

[51] Int. Cl.$^4$ ............................................. C07F 11/00

[52] U.S. Cl. ................................. 556/31; 75/0.5 AA; 252/62.55; 252/62.56; 252/62.57; 252/62.58; 252/62.59; 252/62.6; 252/62.61; 252/62.62; 252/62.63; 252/62.64; 534/16; 556/147

[58] Field of Search ............... 75/0.5 AA; 252/62.55, 252/62.56, 62.57, 62.58, 62.59, 62.6, 62.61, 62.62, 62.63, 62.64; 556/31, 147; 534/16

[56] References Cited

U.S. PATENT DOCUMENTS

| | | | |
|---|---|---|---|
| 3,317,574 | 5/1967 | Morita et al. | 252/62.55 |
| 3,994,819 | 11/1976 | Mollard et al. | 252/62.56 |
| 4,323,596 | 4/1982 | Buxbaum et al. | 252/62.56 |
| 4,367,214 | 1/1983 | Sarnecki et al. | 252/62.56 |
| 4,376,714 | 3/1983 | Pingaud | 252/62.56 |
| 4,400,432 | 8/1983 | Buxbaum et al. | 252/62.56 |
| 4,689,265 | 8/1987 | Miyoshi | 252/62.55 |

Primary Examiner—Wayland Stallard
Attorney, Agent, or Firm—Cushman, Darby & Cushman

[57] ABSTRACT

The disclosed particulate composition of simple or mixed oxalate of ferromagnetic metals is characterized in that it is provided in the form of needle-shaped particles having a length comprised between 0.05 and 0.5 micrometer, with a proportion higher than 60% of particles having a length equal to the average length ±0.1 μm. and an acicular ratio higher than 3, said average length being comprised between 0.15 and 0.35 μm; its preparation and its application are also disclosed.

19 Claims, No Drawings

PARTICULATE COMPOSITIONS OF FERROMAGNETIC METAL OXALATES IN THE FORM OF SUBMICRONIC ACICULAR PARTICLES, THE PREPARATION OF SAME AND APPLICATION THEREOF

The object of the present invention is particulate compositions of ferromagnetic metal oxalates in the form of submicronic acicular particles, the preparation of same and their application in particular as intermediate products in preparation of magnetic powders.

It is known that the industry for manufacturing magnetic recording media (magnetic tapes, tracks, discs, cards, etc.) uses magnetic powders of oxides, alloys or other materials derived from metals.

These powders can be obtained from organic salts and in particular from oxalates; see, for example, U.S. Pat. Nos. 3,317,574, and 3,994,819.

It is known that a particle can be characterized by its dimensions in the longitudinal (length) and transversal (diameter) directions and also by the acicular ratio, which is the ratio of the length to the diameter.

It is generally agreed that, in the above-mentioned field of use, the best results are obtained with particles whose length is between 0.05 and 0.5 micrometer and whose acicular ratio is approximately between 2 and 5.

The density of the recorded data in effect depends on the size of the particles, and the above-indicated values correspond to optimal values since, for lower values, superparamagnetism phenomena can occur and lower the performances.

In U.S. Pat. No. 3,317,574 a method is described which consists of preparing an aqueous solution of a mixture of a mineral salt, a ferromagnetic metal and a carboxylic acid, and then of adding to said solution an orgnic solvent which is capable of causing precipitation of the organic acid salts of the metals present.

Such a method, however, only provides particles having an acicular ratio of close to 2 for the submicronic particles, which is insufficient for certain applications. With the same method it is possible to obtain particles with a higher acicular ratio, but solely for particles whose average length is greater than 1 micrometer.

In U.S. Pat. No. 3,994,819, a method is described which provides, by slow addition of a hydroalcoholic solution of mineral salts of ferromagnetic metals to a hyroalcoholic solution of oxalic acid, particles of oxalates having an average length generally between 0.5 and 1 micrometer, with a relatively low acicular ratio. In the same U.S. patent, a method is described which enables the length of the particles to be decreased, said method consisting of very slowly adding the solution of salts to the solution of oxalic acid in a mixture of ethanol and petroleum ether and by carrying out the precipitation step at $-20°$ C. Particles with an average length equal to 0.4–0.5 micrometer are obtained and the average acicular ratio is approximately equal to 12, which is a little too high. Above all, however, the particles obtained are too heterogeneous for certain applications.

In addition, this method does not enable ferrous sulfate to be used as a starting material: it is necessary to use, at least in part, ferrous chloride, which is more soluble and more expensive, in order to avoid working with excessive amounts of solution.

The present invention resides in the discovery of a new method which, for the first time, provides single or mixed oxalate particles of ferromagnetic metals with dimensions and acicular ratios in accordance with the optimal norms indicated above. The method of the invention further has the advantage of not requiring cooling, of enabling the exclusive use of ferrous sulfate and of being quicker than the prior art methods.

The object of the present invention, therefore, is a particulate composition of single or mixed oxalates of ferromagnetic metals, characterized by the fact that it comprises acicular particles having a length of between 0.05 and 0.5 micrometer, with more than 60% of the particles having a length equal to the average length $\pm 0.1$ micrometer and an acicular ratio of greater than 3, with said average length being between 0.15 and 0.35 micrometer.

In certain cases, the method of the invention even allows particulate oxalate compositions to be prepared, more than 80% of the particles of which, and even sometimes more than 90% of the particles, have said characteristics. It is this high homogeneousness of the particles which constitutes one of the most important characteristics of the invention.

The oxalate particles which are the object of the invention can further have the following characteristics, taken separately or in combination:

The average acicular ratio of the particles varies for example from 3 to 10;

The ferromagnetic metal is selected from among iron, cobalt and nickel;

Said oxalate is a mixed oxalate comprising, in addition to at least one ferromagnetic metal, at least one bivalent metal selected from among copper, zinc, cadmium, magnesium, manganese, the alkaline earth metals (calcium, barium, strontium), europium, ytterbium, tin and lead;

Said oxalate further contains, as an adjuvant or doping agent, one or several elements chosen from among lithium, potassium, aluminum, scandium, titanium, vanadium, chromium, yttrium, zirconium, niobium, molybdenum, bismuth, arsenic, antimony, silicon, germanium, boron, gallium, indium, and trivalent rare earths (for example gadolinium, neodymium, dysprosium, samarium, terbium, cerium, praseodymium, holmium, erbium, thulium, lutetium); the amount of doping agent is a function of the planned use for the final product and is generally less than 3% by weight;

Said oxalate is an iron-based oxalate containing at least 60% of iron atoms in relation to the total of metallic atoms;

Said oxalate corresponds (except for the possible doping agents) to the formula:

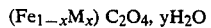

$$(Fe_{1-x}M_x) C_2O_4, yH_2O$$

wherein:

M represents at least one divalent metal selected from among cobalt, nickel, copper, zinc, cadmium, magnesium, manganese, the alkaline earth metals, europium, ytterbium, tin and lead, y is a number greater than or equal to zero and less than or equal to 2, and x is a number less than or equal to $\frac{1}{3}$.

Most frequently, x is less than 0.15.

The object of the invention is also a method for preparation of a particulate oxalate mass, as defined above, said method being characterized by the fact:

that, on the one hand, a solution is prepared containing 0.1 to 1 mole per liter of oxalic acid in a first organic solvent having a dielectric constant of less than 30, said solution possibly containing at most 15% by volume of water;

that, on the other hand, a concentrated solution is prepared of at least one mineral salt of the metal or metals which it is sought to obtain in oxalate form in a liquid medium containing at least 25% by volume of a second organic solvent selected from among methanol, ethanol, tetrahydrofuran, and liquid polyols at room temperature, or mixtures of these solvents, with the possible remainder of said liquid medium being composed of water, the total concentration of the salts being greater than 1 mole/liter, said solution being acidified in order to assist the solubilization of the salts and further containing possible doping agents;

then said salt solution is progressively poured into said oxalic acid solution by stirring the latter, in order to obtain a particulate oxalate precipitate;

it being understood that at least one of said organic solvents is an alcohol.

One of the principal characteristics of the method of the invention is to be able to be used in the presence of a minimum of water, without, however, requiring the use of anhydrous solvents and reagents; for example, the salts and oxalic acid can be used in the hydrate form, and the ethanol used can be the commercially available 95% or even 90% alcohol. It is by using the minimum of water that, in accordance with the method of the invention, very small-sized homogeneous acicular particles can be obtained.

Among the organic solvents capable of rendering the oxalic acid soluble with a minimum of water, or even without water (except for the crystallization water of the oxalic acid), ethanol, 1-propanol, isopropanol, butanol, acetone, ethyl ether, petroleum ether/ethanol mixtures, or even mixtures of these solvents can be cited. The solvents with the lowest dielectric constants will give the smallest size particles.

In order to render the starting salts soluble, it is generally necessary to use an aqueous medium. The quantity of water is, however, decreased by, on the one hand, the addition of the second organic solvent and, on the other hand, by acidifying the medium with an acid such as hydrochloric acid, sulfuric acid, phosphoric acid, acetic acid, etc.

Of course, the acid used must not give a salt which is insoluble with the metals of the starting salts. In addition, the acid stabilizes the ferrous salts, if such are present. In certain cases, it is possible to render the salts soluble practically without water, except for the water constituting the salts and the water present in the commercially available organic solvents, such as ethanol. In particular, a propanol-methanol mixture can be used (see Example 33).

When it is desired to obtain very small-sized particles, for example less than $0.3\mu$, it is desirable to select the second organic solvent (present in the salt solution) with the lowest possible dielectric constant but which, however, is compatible with obtaining a concentrated salt solution. Preferably, water does not represent more than 70% by volume of the solution of starting salts.

The effect of the dielectric constant of the solvents is illustrated in particular in Examples 34 and 36–38 below.

The solvents used for the salt and for the oxalic acid are generally different. However, ethanol, for example, can be used in both cases.

As indicated above, at least one of said first and second organic solvents is an alcohol (mono-alcohol or polyol), as this assists in obtaining acicular particles.

In view of the preceding indications, a further object of the invention is a method, such as defined above, wherein the size of the particles is regulated by the choice of solvents, with the size of the particles being smaller when the dielectric constant of the organic solvents is lower and when water is absent or present in small quantities.

The quantity of oxalic acid used is at least equal to the stoichiometric quantity. It is generally preferred to use a slight excess of oxalic acid, for example on the order of 10% in moles, so as to precipitate to the maximum the metals of the starting salt or salts.

The addition of the salt solution to the oxalic acid solution must be progressive. It must, however, be avoided that this addition takes too long. This is generally carried out in less than thirty minutes, and preferably in 15 minutes or less (for example from 5 to 15 minutes).

In accordance with a preferred embodiment, the oxalic acid solution is stirred and the salt solution is progressively introduced into said stirred solution by pulverizing the salt solution over the oxalic acid solution.

The quantity of doping agent present in the oxalate particles obtained using the method of the invention obviously depends on the solubility of the doping agent in the reaction medium.

It is easy to determine in each case, by simple routine experiments, the quantity of doping agent to be introduced into the reaction medium in order to obtain the desired amount of doping agent in the oxalate particles.

The method of the invention has the advantage of not requiring expensive cooling or of long periods of precipitation which, together with the use of relatively low concentrations, greatly increase the cost of the products prepared in accordance with the prior art methods.

Contrary to the method of U.S. Pat. No. 3,994,819, the method of the present invention enables the use of iron salts solely in the form of ferrous sulfate.

Moreover, the method of the present application can be used at room temperature and with more concentrated solutions which avoids the use of volumes of solution which are too large.

The polyols which can be used to prepare the starting solutions of mineral salts are in general all liquid polyols (in particular diols and triols) at room temperature, which, in possible combination with the water or with the methanol, allow sufficiently concentrated solutions of said mineral salts to be obtained, including the ferrous sulfate (solutions with a concentration greater than 1M, and preferably close to 2M).

Among the polyols which can be used in the method of the present application, ethylene glycol, glycerol, diethylene glycol and propylene glycol, etc., as well as mixtures thereof, or even mixtures of at least one of said polyols with other solvents such as a lower alkanol, can in particular be mentioned.

Among the solvents and mixtures of solvents which can be used to prepare the solution of mineral salts, the following can be mentioned:
propanol-methanol mixtures;
ethanol with 10% water;
propanediol-water mixtures;
tetrahydrofuran-water mixtures;

water-ethylene glycol mixtures containing at least 25% ethylene glycol and pure ethylene glycol;

mixtures containing at least 20% ethylene glycol and at least 20% of another polyol or methanol, with the remainder being water;

water-methanol mixtures containing at least 50% methanol.

Through the use of said solvents, it is possible to increase the concentration of the salts and to decrease the size of the particles obtained, while working at room temperature.

In addition, it has been noted in a surprising manner that it was possible to considerably increase the reaction speed without unfavorably affecting the morphological characteristics of the particles obtained, by carrying out the introduction of the salt solution by pulverizing said solution over the appropriately stirred solution of oxalic acid.

The reaction speed can then be 20 times greater than that obtained with the prior art technique of U.S. Pat. No. 3,994,819.

A further object of the invention is the use of the particulate oxalate compositions obtained in this manner in the preparation of particles of oxides, nitrides, oxynitrides, borides, carbonitrides, oxycarbonitrides, corresponding metals or metal alloys which can be obtained from the oxalates in accordance with known methods; see, for example, British Pat. No. 679,172, U.S. Pat. No. 3,317,574 and French Pat. Nos. 2,180,575 and 2,284,580, etc.

The following inventions illustrate the invention without, however, limiting it.

EXAMPLE 1

A solution A of 0.5 molar oxalic acid was prepared by dissolving 13.75 grams of oxalic acid in 95% by volume ethyl alcohol, at room temperature.

A twice molar solution B was prepared by dissolving 26 grams of iron II sulfate, 1 gram of cobalt II sulfate ($CoSO_4$, $7H_2O$) and 0.7 gram of zinc sulfate ($ZnSO_4$, $7H_2O$) in a mixture containing 60% water and 40% ethylene glycol to which 0.5 ml of HCl 12N was added.

Solution B was introduced by pulverization at a rate of 7 l/hour into the strongly stirred solution B so as to obtain a precipitate of a mixed Fe, Co, Zn oxalate having the formula ($Fe_{0.938}Co_{0.038}Zn_{0.024}$) $C_2O_4$, $2H_2O$.

The pulverization was carried out using a pulverizer enabling drops having an average size of 0.8 mm to be obtained.

After washing and drying of the precipitate, electronic microscopic examination enabled the measurement of the dimensions and the counting of the particles to be carried out. It was noted that more than 90% of the particles had a length of 0.38±0.08 micrometer and a diameter of 0.042±0.01 micrometer.

EXAMPLE 2

A solution A was prepared which was identical to that of Example 1.

A twice molar solution B was prepared by dissolving 25.9 grams of iron II sulfate ($FeSO_4$,$7H_2O$), 0.9 gram of cobalt sulfate ($CoSO_4$, $7H_2O$) and 1.2 g of zinc sulfate ($ZnSO_4$,$7H_2O$) in a mixture containing 30% water and 70% methanol to which 10 ml of hydrochloric acid 12N was added.

Solution B was introduced by pulverization at a rate of 7 l/hour into the strongly stirred solution B so as to obtain a precipitate of a mixed Fe, Co, Zn oxalate having the formula: ($Fe_{0.923}Co_{0.034}Zn_{0.043}$) $C_2O_4$, $2H_2O$.

After washing and drying of the precipitate, electronic microscopic examination enabled the determination that acicular particles had been obtained, more than 80% of which had a length of 0.35±0.10 micrometer and a diameter of 0.05±0.01 micrometer.

EXAMPLE 3

A solution A was prepared which was identical to that of the preceding examples.

A twice molar solution B was prepared by dissolving 25.9 grams of iron II sulfate ($FeSO_4$,$7H_2O$), 0.9 gram of cobalt sulfate ($CoSO_4$, $7H_2O$) and 1.2 grams of zinc sulfate ($ZnSO_4$,$7H_2O$) in a mixture containing 25% water, 25% ethylene glycol and 50% methanol to which 0.5 ml of hydrochloric acid 12N was added.

Solution B was introduced by pulverization at a rate of 7 l/hour into the strongly stirred solution B so as to obtain a precipitate of a mixed Fe, Co, Zn oxalate having the formula:

$$(Fe_{0.923}Co_{0.034}Zn_{0.043}) C_2O_4, 2H_2O.$$

After washing and drying of the precipitate, electronic microscopic examination enabled the determination that acicular particles had been obtained, more than 80% of which had a length of 0.38±0.10 micrometer and a diameter of 0.050±0.015 micrometer.

EXAMPLE 4

A solution A was prepared which was identical to that of the preceding examples.

A twice molar solution B was prepared by dissolving 26 grams of iron II sulfate ($FeSO_4$,$7H_2O$), 1 gram of cobalt sulfate ($CoSO_4$, $7H_2O$) and 0.7 grams of zinc sulfate ($ZnSO_4$,$7H_2O$) in a mixture containing 20% water, 40% ethylene glycol and 40% glycerol, to which 0.5 ml of hydrochloric acid 12N was added.

Solution B was introduced by pulverization at a rate of 7 l/hour into the strongly stirred solution B so as to obtain a precipitate of a mixed Fe, Co, Zn oxalate having the formula:

$$(Fe_{0.938}Co_{0.038}Zn_{0.024}) C_2O_4, 2H_2O.$$

After washing and drying of the precipitate, electronic microscopic examination enabled the determination that acicular particles had been obtained, more than 85% of which had a length of 0.37±0.10 micrometer and a diameter of 0.048±0.015 micrometer.

Mixed acicular oxalates with identical dimensions to those indicated above can be obtained by using iron, cobalt and zinc chlorides in the place of the sulfates.

EXAMPLE 5

The method of Example 1 was used, except that in solution B, 1.4 g of $MnCl_2$, $6H_2O$ was further added. Particles were obtained whose composition corresponds to the formula:

$$(Fe_{0.872}Co_{0.038}Zn_{0.024}Mn_{0.066}) C_2O_4, 2H_2O.$$

The sizes of the particles were similar to those of the particles of Example 1.

EXAMPLE 6

The method of Example 1 was used, but replacing the ferrous sulfate with 19.9 g of $FeCl_2$, $4H_2O$, and in addition 2 g of $BaCl_2$ was added to solution B. Oxalate particles were obtained corresponding to the formula:

$$(Fe_{0.925}Co_{0.038}Zn_{0.024}Ba_{0.013})\ C_2O_4,\ 2H_2O.$$

The sizes of the particles were similar to those of the particles of Example 1.

EXAMPLE 7

The method of Example 2 was used, but in addition 0.16 g of $Eu(No_3)_2$ was added to solution B. Oxalate particles were obtained having the formula:

$$(Fe_{0.915}Co_{0.034}Zn_{0.043}Eu_{0.008})\ C_2O_4,\ 2H_2O.$$

The sizes of the particles were similar to those of the particles of Example 2.

EXAMPLE 8

The method of Example 1 was used, but in addition 0.45 g of $TiCl_3$ was added to solution B. Oxalate particles were obtained corresponding (except for the titanium oxalate doping agent) to the formula given in Example 1. These particles contained 0.25% by weight of titanium.

The sizes of the particles were similar to those of the particles of Example 1.

EXAMPLE 9

The method of Example 1 was used, but in addition 3 g of $SbCl_3$ were added to solution B. Oxalate particles were obtained corresponding (except for the antimony oxalate doping agent) to the formula given in Example 1. These particles contained 0.15% by weight of antimony.

The sizes of the particles were similar to those of the particles of Example 1.

EXAMPLE 10

The method of Example 1 was used, but in addition 0.45 g of $TiCl_3$ and 1.5 g of $AlCl_3$ were added to solution B. Oxalate particles were obtained corresponding (except for the titanium and aluminum oxalate doping agent) to the formula given in Example 1. These particles contained 0.05% by weight of titanium and 0.7% of aluminum.

The sizes of the particles were similar to those of the particles of Example 1.

The method of Example 1 was used, but in addition 0.5 g of $VCl_3$ was added to solution B. Oxalate particles were obtained corresponding (except for the vanadium oxalate doping agent) to the formula given in Example 1. These particles contained 1.2% by weight of vanadium.

The sizes of the particles were similar to those of the particles of Example 1.

EXAMPLE 12

The method of Example 1 was used, but in addition 0.3 g of KCl was added to solution B. Oxalate particles were obtained corresponding (except for the potassium oxalate doping agent) to the formula given in Example 1. These particles contained 0.3% by weight of potassium.

The sizes of the particles were similar to those of the particles of Example 1.

The method of Example 2 was used, but in addition 0.5 g of $YbCl_2$ was added to solution B. Oxalate particles were obtained corresponding (except for the ytterbium oxalate doping agent) to the formula given in Example 2. These particles contained 2% by weight of ytterbium.

The sizes of the particles were similar to those of the particles of Example 2.

EXAMPLE 14

The method of Example 2 was used, but in addition 0.5 g of $GdCl_3$, $6H_2O$ was added to solution B. Oxalate particles were obtained corresponding (except for the gadolinium oxalate doping agent) to the formula given in Example 2. These particles contained 2.8% by weight of gadolinium.

The sizes of the particles were similar to those of the particles of Example 2.

The method of Example 2 was used, but in addition 0.5 g of $DyCl_3$ was added to solution B. Oxalate particles were obtained corresponding (except for the dysprosium oxalate doping agent) to the formula given in Example 2. These particles contained 2.7% by weight of dysprosium.

The sizes of the particles were similar to those of the particles of Example 2.

EXAMPLE 16

A solution A of 0.5 molar oxalic acid was prepared by dissolving 13/75 g of oxalic acid in ethyl alcohol at 95% by volume, at room temperature.

A twice molar solution B was prepared by dissolving, in a mixture containing 60% water and 40% ethylene glycol, the following salts:

| | |
|---|---|
| $FeCl_2$, $4H_2O$ | 18.7 g |
| $CoCl_2$, $6H_2O$ | 1 g |
| $ZnCl_2$ | 0.5 g |
| $BaCl_2$ | 0.8 g |

0.5 cm$^3$ of an aqueous solution of hydrochloric acid 12N was added to the mixture. Solution B was introduced into the strongly stirred solution A by pulverization of solution B over solution A at a rate of 7 liters/h, using a pulverizer enabling drops of 0.8 mm on average to be obtained.

The oxalate particles which precipitated were washed and dried.

Oxalate particles were obtained having the formula:

$$(Fe_{0.9391}Co_{0.0420}Zn_{0.0124}Ba_{0.0064})^{2+}C_2O_4{}^{2-}2\text{-}H_2O.$$

EXAMPLES 17 TO 29

In a similar manner, particulate compositions of oxalates were prepared having the following compositions:

EXAMPLE 17

$$(Fe_{0.9393}Co_{0.0430}Zn_{0.0147}Ba_{0.0034})^{2+}C_2O_4{}^{2-}2\text{-}H_2O.$$

EXAMPLE 18

$$(Fe_{0.9335}Co_{0.0433}Zn_{0.0108}Ba_{0.0124})^{2+}C_2O_4{}^{2-}2\text{-}H_2O.$$

EXAMPLE 19

$(Fe_{0.9450}Co_{0.0437}Ba_{0.0112})^{2+}C_2O_4{}^{2-}2H_2O.$

EXAMPLE 20

$(Fe_{0.9342}Co_{0.0435}Zn_{0.0112}Ba_{0.0111})^{2+}C_2O_4{}^{2-}2H_2O.$

EXAMPLE 21

$(Fe_{0.9300}Co_{0.0437}Zn_{0.0263})^{2+}0.9929^{Dy3}+0.0047C_2O_4{}^{2-}2H_2O.$

EXAMPLE 22

$(Fe_{0.9368}Co_{0.0432}Zn_{0.0135}Ba_{0.0065})^{2+}0.9907^{Dy3}+0.0062C_2O_4{}^{2-}2H_2O.$

EXAMPLE 23

$(Fe_{0.9253}Co_{0.0442}Zn_{0.0264}Yb_{0.0041})^{2+}C_2O_4{}^{2-}2H_2O.$

EXAMPLE 24

$(Fe_{0.9296}Co_{0.0438}Zn_{0.0266})^{2+}0.9927^{Gd3}+0.0049C_2O_4{}^{2-}2H_2O.$

EXAMPLE 25

$(Fe_{0.9147}Co_{0.0482}Zn_{0.0334}Eu_{0.00375})^{2+}C_2O_4{}^{2-}2H_2O.$

EXAMPLE 26

$(Fe_{0.9237}Co_{0.0438}Zn_{0.0325})^{2+}0.9972^{Sb3}+0.0018C_2O_4{}^{2-}2H_2O.$

EXAMPLE 27

$(Fe_{0.9336}Co_{0.0390}Zn_{0.0274})^{2+}0.9688^{V3}+0.0131^{Ti4}+0.0058C_2O_4{}^{2-}2H_2O.$

EXAMPLE 28

$(Fe_{0.9324}Co_{0.0456}Zn_{0.0221})^{2+}0.9561^{Ga3}+0.0216^{Ti4}+0.0058C_2O_4{}^{2-}2H_2O.$

EXAMPLE 29

$(Fe_{0.9348}Co_{0.0412}Zn_{0.0150})^{2+}0.9500^{Al3}+0.0334C_2O_4{}^{2-}2H_2O.$

In these examples, the dysprosium was introduced in the form of $DyCl_3$; the ytterbium in the form of $YbCl_2$; the gadolinium in the form of $GdCl_3$; the europium in the form of $Eu(No_3)_2$; the antimony in the form of $SbCl_3$; the titanium in the form of $TiCl_3$; the vanadium in the form of $VCl_3$; the gallium in the form of $Ga_2(SO_4)_3$; and the aluminum in the form of $AlCl_3$.

In addition, the oxalate particles of Example 20 were doped with boron by contacting them with an aqueous solution with 3% by weight of boric acid, at a rate of 50 ml of said solution for 15 g of oxalate.

An oxalate was obtained which corresponded to the formula:

$(Fe_{0.9342}Co_{0.0435}Zn_{0.0112}Ba_{0.0111})^{2+}C_2O_4{}^{2-}2H_2O+0.0249$ mole of $H_3BO_3$

EXAMPLE 30—Iron oxalate

A solution A of 0.5 molar oxalic acid was prepared by dissolving 13.75 grams of oxalic acid in 95% by volume ethyl alcohol, at room temperature.

A twice molar solution B was prepared by dissolving 27.8 grams of iron II sulfate ($FeSO_4$, $7H_2O$) in a mixture containing 60% water and 40% 1,2-propanediol to which 1 ml of HCl 12N was added.

Solution B was introduced dropwise at a rate of 0.8 liter/hour into the strongly stirred solution B so as to obtain an iron oxalate precipitate After washing and drying of the precipitate, electronic microscopic examination enabled the determination to be made that acicular particles had been obtained, more than 60% of which had a length of $0.27\pm0.1$ μm and a diameter of 0.06 μm$\pm0.02$ μm and an average acicular ratio of 5.2.

EXAMPLE 31—Mixed oxalate

A solution A was prepared which was identical to that of the preceding example.

A twice molar solution B was prepared by dissolving 18.4 g of $FeCl_2$, $4H_2O$, 9.96 g of $CoCl_2$, $6H_2O$, 0.45 g of $ZnCl_2$ and 0.8 g of $BaCl_2$ in a mixture containing 60% water and 40% 1,2-propanediol to which 1 ml of HCl 12N was added.

Solution B was added to solution A as above so as to obtain a mixed oxalate precipitate having the formula:

$[Fe_{0.937}Co_{0.043}Zn_{0.013}Ba_{0.07}] C_2O_4, 2H_2O$

After washing and drying of the precipitate, electronic microscopic examination enabled the determination to be made that acicular particles had been obtained, more than 80% of which had a length of $0.25\pm0.1$ μm and 60% had a diameter of 0.075 μm$\pm0.02$ μm and an average acicular ratio of 3.6.

EXAMPLE 32—Iron oxalate

A solution A was prepared which was identical to that of the preceding example.

A twice molar solution B was prepared by dissolving 19.9 g of $FeCl_2$, $4H_2O$ in a mixture containing 60% water and 40% 1,2-propanediol to which 0.5 ml of HCl 12N was added.

Solution B was added to solution A as above so as to obtain an iron oxalate precipitate.

After washing and drying of the precipitate, electronic microscopic examination enabled the determination to be made that acicular particles had been obtained, more than 60% of which had a length of $0.26\pm0.1$ μm and 60% had a diameter of 0.043 μm$\pm0.02$ μm and an average acicular ratio of 6.4.

EXAMPLE 33—Iron oxalate

A solution A was prepared which was identical to that of the preceding example.

A twice molar solution B was prepared by dissolving 19.9 g of $FeCl_2$, $4H_2O$ in a mixture containing 50%

1-propanol and 50% methanol to which 1.5 ml of HCl 12N was added.

Solution B was added to solution A as above so as to obtain an iron oxalate precipitate.

After washing and drying of the precipitate, electronic microscopic examination enabled the determination to be made that acicular particles had been obtained, more than 60% of which had a length of 0.20±0.1 μm and a diameter of 0.06 μm±0.02 μm and an average acicular ratio of 3.7.

EXAMPLE 34—Iron oxalate

A solution A was prepared from 0.5 molar oxalic acid by dissolving 13.75 g of oxalic acid in 1-butanol at room temperature.

A 1.5 molar solution B was prepared by dissolving 19.9 g of FeCl$_2$, 4H$_2$O in a mixture containing 90% ethanol and 10% water to which 1.5 ml of HCl 12N was added.

Solution B was added to solution A as above so as to obtain an iron oxalate precipitate.

After washing and drying of the precipitate, electronic microscopic examination enabled the determination to be made that acicular particles had been obtained, more than 70% of which had a length of 0.17±0.1 μm and a diameter of 0.04 μm±0.02 μm and an average acicular ratio of 4.6.

EXAMPLE 35—Iron oxalate

A solution A was prepared which was identical to that of Example 1.

A twice molar emulation B was prepared by dissolving 19.9 g of FeCl$_2$, 4H$_2$O in a mixture containing 60% water and 40% tetrahydrofuran (THF) to which 0.5 ml of HCl 12N was added.

Solution B was added to solution A as above so as to obtain an iron oxalate precipitate.

After washing and drying of the precipitate, electronic microscopic examination enabled the determination to be made that acicular particles had been obtained, more than 70% of which had a length of 0.22±0.1 μm and a diameter of 0.045 μm±0.02 μm and an average acicular ratio of 5.2.

EXAMPLE 36

The method of Example 34 was used, but replacing the butanol (as solvent for the oxalic acid) with ethanol. Iron oxalate particles were obtained with an average length of 0.27±0.1 μm and an average diameter of 0.038 μm.

The method of Example 34 was used, but replacing the butanol with 1-propanol. Iron oxalate particles were obtained with an average length of 0.24±0.1 μm and an average diameter of 0.055 μm.

EXAMPLE 38

The method of Example 34 was used, but replacing, in the salt solution, the ethanol with propanediol (in other words, a propanediol-water mixture with 90% propanediol was used).

Iron oxalate particles were obtained with an average length of 0.31±0.1 μm and an average diameter of 0.046 μm.

We claim:

1. A particulate composition of single or mixed oxalates of ferromagnetic metals, characterized by the fact that it comprises acicular particles having a length of between 0.05 and 0.5 micrometer, with an amount of more than 60% of the particles having a length equal to the average length ±0.1 μm and an acicular ratio of greater than 3, with said average length being between 0.15 and 0.35 μm.

2. The particulate composition of claim 1, wherein said amount is greater than 80%.

3. The particulate composition of claim 1, wherein the ferromagnetic metal is selected from among iron, cobalt and nickel.

4. The particulate composition of claim 1, wherein said oxalate is a mixed oxalate comprising, in addition to at least one ferromagnetic metal, at least one bivalent metal selected from the group consisting of copper, zinc, cadmium, magnesiuj, manganese, an alkaline earth metal, europium, ytterbium, tin and lead.

5. The particulate composition of claim 1, wherein said oxalate further contains, as an adjuvant or doping agent, one or several elements selected from the group consisting of lithium, potassium, aluminum, scandium, titanium, vanadium, chromium, yttrium, zirconium, niobium, molybdenum, bismuth, arsenic, boron, antimony, silicon, germanium, gallium, indium and a trivalent rare earth.

6. The particulate composition in accordance with claim 5, wherein the doping agent is present in an amount generally less than 3% by weight.

7. The particulate composition of claim 1, wherein said oxalate is an iron-based oxalate containing at least 60% of iron atoms in relation to the total of metallic atoms.

8. The particulate composition of claim 1, wherein said oxalate corresponds (except for the possible doping agents) to the formula:

$$(Fe_{1-x}M_x) C_2O_4, yH_2O$$

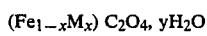

wherein:
M represents at least one metal selected from among cobalt, nickel, copper, zinc, cadmium, magnesium, manganese, the alkaline earth metals, europium, ytterbium, tin and lead,
y is a number greater than or equal to zero and less than or equal to 2,
and x is a number less than or equal to ⅓.

9. The particulate composition in accordance with claim 8, wherein x is less than 0.15.

10. The particulate composition of claim 4 wherein said alkaline earth metal is calcium, barium or strontium.

11. The particulate composition of claim 5 wherein said rare earth is gadolinium, neodymium, hysprosium, samarium, terbium, cerium, praseodymium, holmium, erbium, thulium or lutetium.

12. A process for preparing a particulate composition of single or mixed oxalates of ferromagnetic metals comprising acicular particles having a length of between 0.05 and 0.5 micrometer, with an amount of more than 60 percent of the particles having a length equal to the average length ±0.1 μm and an acicular ratio of greater than 3, with said average length being between 0.15 and 0.35 μm, said process comprising (1) preparing an oxalic acid solution containing 0.1 to 1 mole per liter of oxalic acid in a first organic solvent having a dielectric constant of less than 30, said oxalic acid containing no water or at most 15 percent by volume of water;

(2) preparing an acidified concentrated solution of at least one mineral salt of the metal or metals which it is sought to obtain in oxalate form in an aqueous or non-aqueous liquid medium containing at least 25 percent by volume of a second organic solvent selected from the group consisting of methanol, ethanol, tetrahydrofuran, a polyol which is liquid at room temperature, and a mixture thereof, the total concentration of said mineral salt in said concentrated solution being greater than 1 mole/liter; and (3) progressively pouring said concentrated solution of at least one metal salt into said oxalic acid solution with stirring so as to obtain a particulate oxalate precipitate, with the proviso at least one of said first and second organic solvents is an alcohol.

13. The process of claim 12 which includes incorporating a doping agent in said concentrated solution of at least one metal salt.

14. The process of claim 12 wherein said first organic solvent is selected from the group consisting of ethanol, 1-propanol, isopropanol, butanol, acetone, ethyl ether and a petroleum ether/ethanol mixture.

15. The process of claim 12 wherein said oxalic acid solution is stirred and said concentrated solution of at least one metal salt is progressively introduced into said stirred oxalic acid solution by pulverizing said concentrated solution of at least one metal salt over said oxalic acid solution.

16. The process of claim 12 wherein said liquid polyol is selected from the group consisting of ethylene glycol, glycerol, diethylene glycol and propylene glycol.

17. The process of claim 16 wherein said polyol is in admixture with water, a lower alkanol or a mixture of water and a lower alkanol.

18. The process of claim 12 wherein said liquid medium comprises
  (i) a propanol-methanol mixture,
  (ii) ethanol with 10 percent water,
  (iii) a propanediol-water mixture,
  (iv) a tetrahydrofuran-water mixture,
  (v) a water-ethylene glycol mixture containing at least 25% ethylene glycol, and pure ethylene glycol,
  (vi) a mixture containing at least 20% ethylene glycol and at least 20% of a polyol other than ethylene glycol or of methanol, the remainder being water, or
  (vii) a water-methanol mixture containing at least 50% methanol.

19. The process of claim 12 wherein the size of the particles is regulated by the selection of said organic solvents, with the size of said particles being smaller when the dielectric constant of said organic solvents is lower and water is absent or is present in small quantities.

* * * * *